US00PP32920P2

(12) United States Plant Patent
Hansen

(10) Patent No.: US PP32,920 P2
(45) Date of Patent: Mar. 23, 2021

(54) ***SALVIA* PLANT NAMED 'BACK TO THE FUCHSIA'**

(50) Latin Name: ***Salvia* hybrid**
Varietal Denomination: Back to the Fuchsia

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,810

(22) Filed: Jul. 14, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt

(57) ABSTRACT

The new and distinct cultivar of perennial *Salvia* plant named 'Back to the Fuchsia' characterized by its medium-sized, dark-pink flowers from deep purplish-red buds densely arranged in verticils and dark greyish-red calyxes and stems with intense light. The new plant has a medium height, compact, rounded habit with stiff, upright, heavily-branched stems and a strong vigorous growth rate and gray-green foliage. 'Back to the Fuchsia' is useful for landscaping as a specimen plant or en masse.

2 Drawing Sheets

Botanical denomination: *Salvia* hybrid.
Cultivar designation: 'Back to the Fuchsia'.

STATEMENT REGARDING PRIOR DISCLOSURES UNDER 37 CFR 1.77(b)(6)

The first non-enabling disclosure of the new plant, in the form of a photograph and brief description on a website maintained by Walters Gardens, Inc. first posted on Dec. 1, 2019. Subsequently, the new plant was advertised in the "Walters Gardens 20-21 Catalog" first distributed on May 20, 2020. The claimed plant was first sold on Sep. 30, 2019 by Goetjes Allplant BV of The Netherlands who obtained the plant and all information relating thereto, from the inventor. Walters Gardens, Inc. obtained the new plant and all information on the new plant from the inventor. No plants of *Salvia* 'Back to the Fuchsia' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of perennial *Salvia* plant hereinafter referred to by the cultivar name *Salvia* 'Back to the Fuchsia' or as the new plant. The new plant was selected from a block of seedlings resulting from an insect pollination in late spring of 2014 with the unreleased, proprietary hybrid known as "13-24-1 x OP" as the female or seed parent and the male or pollen parent is unidentified sibling of "13-24-1 x OP" in an isolation block at a wholesale perennial nursery in Zeeland, Mich., USA. Seed was collected on Jun. 11, 2014 and sown at the same nursery. The new plant was initially evaluated in the summer of 2016 and assigned the breeder code 14-10-2 through the trial process prior to assigning a cultivar name.

The new *Salvia* was further evaluated and asexually propagated initially by division and later by basal cuttings taken at the same nursery in Zeeland, Mich., USA in 2016. Evaluation of these and further cutting grown plants shows that *Salvia* 'Back to the Fuchsia' continues to be stable and produce true to type plants in successive generations of asexual propagation.

SUMMARY OF THE INVENTION

Plants of *Salvia* 'Back to the Fuchsia' have not been observed under all possible environmental conditions. The phenotype may vary somewhat with variations in environment such as temperature, nutrition and light intensity without, however, any variance in genotype.

*Salvia* 'Back to the Fuchsia' can be closely compared to *Salvia* 'Moulin Rouge' U.S. Plant Pat. No. 32,387, 'Pink Profusion' U.S. Plant Pat. No. 31,435, 'Pink Dawn' U.S. Plant Pat. No. 26,343, and 'Bumbleberry' U.S. Plant Pat. No. 31,602. 'Moulin Rouge' has flowers that are more rosy pink on similar size plants. 'Pink Profusion' has a shorter habit with fewer and smaller flowers per inflorescence of a slightly different hue of violet. 'Pink Dawn' has a slightly shorter habit and flowers that are larger in size and cotton candy pink in color. 'Bumbleberry' has significantly shorter habit and flowers of dark fuchsia-pink with dark wine purple buds. The female parent, "13-24-1 x OP" was not maintained in photography or plants so no comparison is possible. Comparison with the male parent is not possible as the exact plant is not known.

The following characteristics in combination distinguish *Saliva* 'Back to the Fuchsia' as a new and distinct cultivar from all other cultivars known to the inventor:

1. Medium-sized dark-pink flowers densely arranged in verticils;
2. Stiff, upright, heavily, compound-branched stems;
3. Deep purplish-red flower buds;

4. Medium height, compact, rounded, strong, vigorous and winter-hardy habit;
5. Rugose olive-green foliage.

BRIEF DESCRIPTION OF THE DRAWINGS

The photographs of the new plant demonstrate the unique traits and the overall appearance of *Salvia* 'Back to the Fuchsia'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed.

DETAILED BOTANICAL DESCRIPTION

Figure 1:
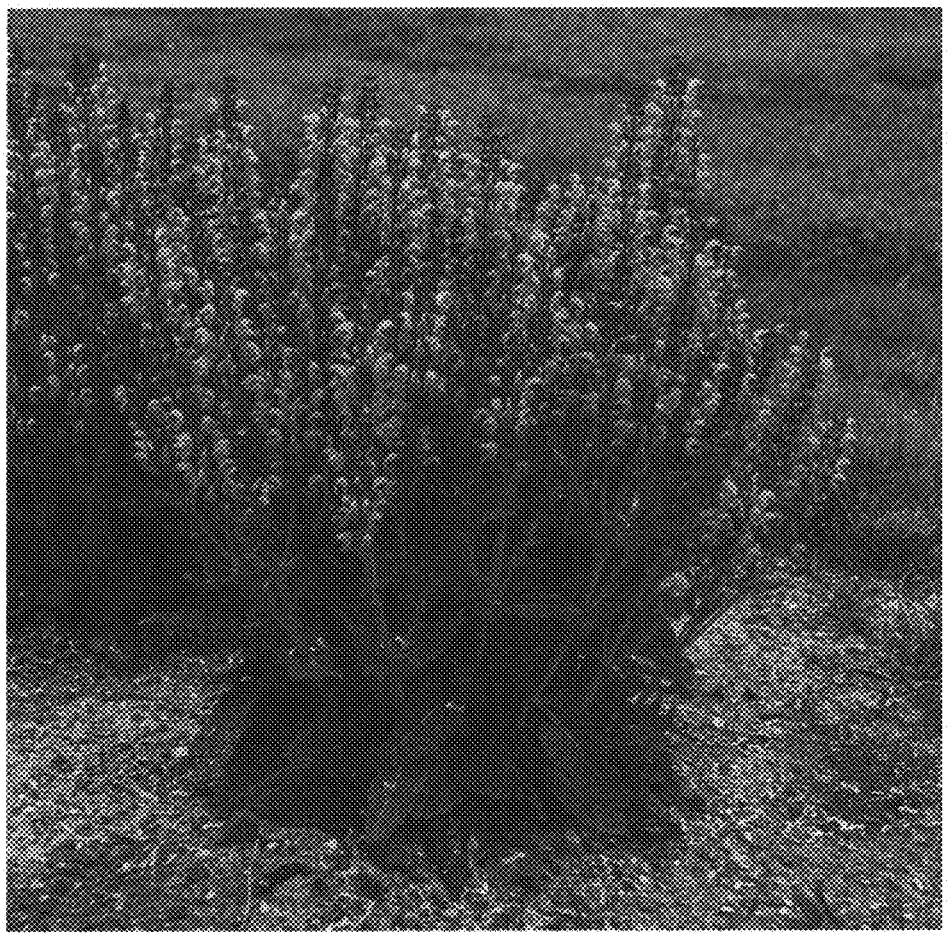
FIG. 1 shows the plant habit in full flower in a landscape.
Figure 2:
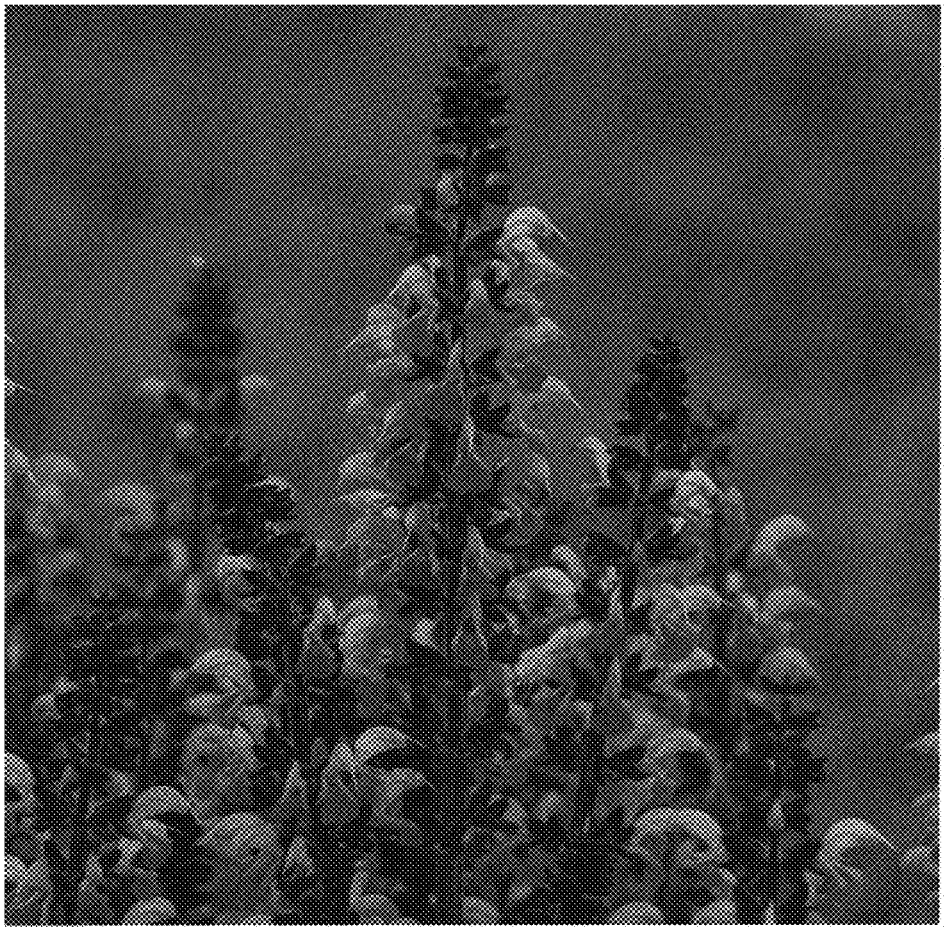
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Back to the Fuchsia' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in an outdoor full-sun trial garden at a wholesale perennial nursery in Zeeland, Mich. Plants were given supplemental water and fertilizer and plant growth regulators were used for the greenhouse trials only.

Botanical classification: *Salvia* hybrid;

Parentage: Female or seed parent was the proprietary hybrid "13-24-1 x OP"; male or pollen parent was an unknown sibling of "13-24-1 x OP";

Plant habit: Winter-hardy herbaceous perennial; multi-stemmed, compact, rounded, with mostly basal foliage, and flowers in several tightly arranged verticils on branched upright racemes displayed above foliage; in flower with panicles about 52 cm tall and about 84 cm wide at the fullest point; cauline foliage extends up the stems about 30 cm; about 15 to 18 branched flowering panicles per plant;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color;

Foliage: Opposite; simple; slightly rugose; deltoid becoming lanceolate distally; margin irregularly doubly crenate and micro-ciliolate; adaxial surface glabrous, and abaxial puberulent; acute apex and base cordate to truncate; leaf blades to about 11.0 cm long and 6.5 cm across, decreasing in size distally; average about 8.5 cm long and 5.0 cm across; faint sage fragrance;

Foliage color: Young adaxial surface nearest RHS 146B, young abaxial surface between RHS 146C and RHS 146B; mature adaxial nearest NN137A, mature abaxial between RHS 137B and RHS 138A;

Venation: Reticulate; impressed on adaxial side and costate on abaxial side; pubescent abaxial, micro-puberulent adaxial;

Vein color: Adaxial midrib nearest RHS 145C; adaxial primary and secondary veins nearest RHS 147D; abaxial midrib nearest RHS 145D; abaxial primary veins nearest RHS 145D and secondary veins gradually darkening to nearest RHS 145C toward leaf margin;

Petiole: Slightly concavo-convex; pubescent to glandular; to about 12.0 cm long and 8.0 mm wide at base, average 7.5 cm long and 6.0 mm wide at base;

Petiole color: Adaxial distally nearest RHS 138C and proximally RHS 138B with slight blush of and RHS N77B; abaxial distally nearest 145D and proximally between RHS 145C moderately blushed with RHS N77B;

Flower description: Perfect; bilabiate; zygomorphic; fused corolla portion glabrous adaxial and puberulent abaxial;

Flower size: 18.0 mm long to tip of exserted stigma, 10.0 mm tall, 6.0 mm wide; corolla 14.0 mm long, 10.0 mm tall and 6.0 mm wide; corolla fused in basal portion 8.0 mm long, 4.5 mm tall and 2.5 mm wide;

Inflorescence: Panicle; branched at about 45° angle, typically compound branched; branches to 28 cm long and 3.0 mm across base; flowering portion 22 cm tall and 22 cm across; verticillate with flowering generally beginning at lower verticils and advancing up the scape, but not all flowers at each verticil opening at the same time giving the effect of a scape being in continuous flower for longer periods; typically six flowers per verticil; average distance between verticils about 9.3 mm, greater proximally and less distally; about 14 verticils per main branch; about 250 to 400 flowers per panicle;

Flowering period: Flowering beginning late spring for about six weeks and repeating if initial inflorescences removed;

Peduncle: Quadrangular; pubescent to glandular; to 45.0 cm long and 6.0 mm across at base;

Peduncle color: Proximal portion nearest RHS 146D with sections strongly blushed to solid nearest RHS 187A, and distally nearest RHS 146B with blushing nearest RHS 187A becoming solid nearest RHS N186C;

Flower attitude: Flower midline projected about 10 degree angle above horizontal and hood petal about 45 degree angle above horizontal;

Flower longevity: About four days on the plant or as cut flower; self-cleaning, petals not persistent;

Flower fragrance: None detected under present growing conditions;

Flower buds one day prior to anthesis: Arcuate dorsally, flat ventrally and flattened slightly laterally; with rounded apex; micro-puberulent; about 9.0 mm long, 5.0 mm tall and 3.5 mm wide;

Bud color: Exposed petals nearest RHS 71A; abaxial calyx nearest RHS N186C;

Petals: Bilabiate corolla; upper hood lip and lower lip (labium) with three lobes;

Hood (upper) petal: Micro-puberulent to micro-glandular abaxial, glabrous adaxial; about 14.0 mm long, 3.0 mm tall and 2.5 mm across; folded distally along longitudinal axis; apex rounded and emarginate, with 0.5 mm deep notched apex and base fused with labium in proximal 8.0 mm;

Hood color: Adaxial nearest RHS 71B, abaxial nearest RHS 71B;

Labium (lower) petal: Consisting of three lobes, two proximal side lobes and larger center lobe;

*Center lobe*.—Obcordate, cupped; truncate base and emarginate apex with notch about 1.0 mm deep; margin slightly crenulate; puberulent in 5 mm of abaxial base before tube, glabrous adaxial and distal abaxial; size about 11.0 mm long (including fused base) extending 3.0 mm beyond fusion point; natural width 4.0 mm and when spread to 5.0 mm.

Center lobe color: Adaxial nearest RHS 71B and abaxial nearest RHS 71B;

Side lobes: Oblong to oblanceolate; apices rounded; base fused to corolla tube; slightly twisted; glabrous adaxial and abaxial; size about 3.5 mm long from fusion and 1.0 mm wide;

Side lobes color: Nearest RHS 71B adaxial and abaxial;

Corolla tube base color:

Androecium: Two, fused with labium, contained within hood petal except when triggered by pollinator;

*Filament*.—Glabrous, fused about 4.0 mm from base of labium petal; arcuate around inside of hood petal; about 9.0 mm long and less than 0.5 mm diameter, free in distal 5.0 mm, with a 1.0 mm long trip mechanism longitudinally folded at base; color of filament nearest RHS 64B at base and distally nearest RHS 64D; color of trip mechanism nearest RHS 64B.

*Anther*.—Glabrous; oblong ellipsoidal; dorsifixed; longitudinal; about 1.0 mm long and 0.5 mm diameter; color nearest RHS N187A.

*Pollen*.—Abundant; less than 0.1 mm circumference; color nearest RHS 13A.

Gynoecium: One, arcuate around inside of hood petal;

*Style*.—Exserted; about 19.0 mm long and 0.5 mm diameter; color nearest RHS 69D at base, transitioning distally about 2.0 mm before stigma split to nearest RHS 70A.

*Stigma*.—Bifurcate and curved in the terminal 1.5 mm; about 0.2 mm diameter; apex acute; color nearest RHS 70A.

*Ovary*.—Superior; four seeded; color nearest RHS 163B.

Fruit: Nutlet, one to four per flower; globose; about 2.0 mm diameter; color darker than RHS 200A;

Calyx: Campanulate; fused in basal 5.0 mm; tube about 9.0 mm long and 5.0 mm tall at mouth and 4.0 mm wide; lower set bifurcate in distal 0.5 mm; upper set of trifurcate in distal 1.0 mm;

Sepals: Five, three upper and two lower; linear; acute apex; fused in basal 4.0 mm;

Sepal color: Adaxial nearest RHS 146C with veins nearest RHS 137C; abaxial variable with light intensity, high light producing nearest RHS N186C with veins also nearest RHS N186C, and in lower light nearest RHS 137B with veins nearest RHS N186C;

Bracts: Each verticil subtended by two opposite deltoid bracts; apex narrowly acute to acuminate, base sessile and truncate, margin crenate; glabrous adaxial and pubescent abaxial; bract size up to 20.0 mm long and 18.0 mm wide, decreasing distally;

Bract color: Variable with light intensity, in lower light adaxial surfaces between RHS 137A and RHS NN37A with midrib nearest RHS 145D, abaxial nearest RHS NN137C with midrib of nearest RHS 145D; color with more intense light exposure blushed with nearest RHS N186C; on both surfaces;

Pedicels: Cylindrical; puberulent to glandular; to about 4.0 mm long and 0.7 mm diameter; slightly upwardly at flower anthesis;

Pedicel color: Variable with light intensity, high light exposure nearest RHS N186C, low light exposure nearest RHS 144B;

Culture: Plants of *Salvia* 'Back to the Fuchsia' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Back to the Fuchsia' as herein described and illustrated.

* * * * *